(12) United States Patent
Gross et al.

(10) Patent No.: US 11,974,981 B2
(45) Date of Patent: May 7, 2024

(54) METHODS AND COMPOSITIONS FOR TREATING ENDOMETRIOSIS AND ENDOMETRIOSIS ASSOCIATED SYMPTOMS

(71) Applicant: The Board of Trustees of the Leland Stanford Junior University, Stanford, CA (US)

(72) Inventors: Eric Gross, Menlo Park, CA (US); Daria Mochly-Rosen, Menlo Park, CA (US); Stacy Lynn McAllister, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/681,591

(22) Filed: Feb. 25, 2022

(65) Prior Publication Data
US 2022/0233498 A1    Jul. 28, 2022

Related U.S. Application Data

(63) Continuation of application No. 16/609,413, filed on Oct. 29, 2019, now abandoned, which is a continuation of application No. PCT/US2018/030924, filed on May 3, 2018.

(60) Provisional application No. 62/643,591, filed on Mar. 15, 2018, provisional application No. 62/502,310, filed on May 5, 2017.

(51) Int. Cl.
| | |
|---|---|
| *A61K 31/36* | (2006.01) |
| *A61K 9/00* | (2006.01) |
| *A61K 9/06* | (2006.01) |
| *A61P 29/00* | (2006.01) |

(52) U.S. Cl.
CPC ............ *A61K 31/36* (2013.01); *A61K 9/0024* (2013.01); *A61K 9/06* (2013.01); *A61P 29/00* (2018.01)

(58) Field of Classification Search
CPC ....................................................... A61K 31/36
USPC ........................................................... 514/466
See application file for complete search history.

(56) References Cited

U.S. PATENT DOCUMENTS

| | | | |
|---|---|---|---|
| 2010/0113423 A1 | 5/2010 | Mochly-Rosen et al. | |
| 2015/0182495 A1 | 7/2015 | Zambelli et al. | |
| 2017/0057982 A1 | 3/2017 | Yang et al. | |

OTHER PUBLICATIONS

Budas et al., J. Mol. And Cellul. Cardiol. (2010) vol. 48, pp. 757-764.*
Laux-Biehlmann et al. (2015) "Menstruation pulls the trigger for inflammation and pain in endometriosis" Tren'ds in Pharmacological Sciences, vol. 36, pp. s270-276.
Olive et al. (2001) "Treatment of Endometriosis" New England Journal of Medicine, Massachusetts Medical Society. US. vol. 345. No. 4, pp. 266-275.
Zambelli et al. (2014) "Aldehyde dehydrogenase-2 regulates nociception in rodent models of acute inflammatory pain", Science Translational Medicine, vol. 6. No. 251, pp. 251ra118-251ra118.

* cited by examiner

*Primary Examiner* — Taofiq A Solola
(74) *Attorney, Agent, or Firm* — Pamela J. Sherwood; Bozicevic, Field & Francis LLP

(57) ABSTRACT

Methods and compositions are provided for treating endometriosis in an individual, and the pain associated with endometriosis. Aspects of the methods include administering to the individual an agent that promotes ALDH activity.

18 Claims, 7 Drawing Sheets

METHODS AND COMPOSITIONS FOR TREATING ENDOMETRIOSIS AND ENDOMETRIOSIS ASSOCIATED SYMPTOMS

CROSS REFERENCE TO RELATED APPLICATIONS

This application is a Continuation of U.S. application Ser. No. 16/609,413, filed Oct. 29, 2019, which claims the benefit of PCT Application No. PCT/US2018/030924, filed May 3, 2018, which claims the benefit of U.S. Provisional Application No. 62/643,591, filed Mar. 15, 2018, and U.S. Provisional Application No. 62/502,310, filed May 5, 2017. The contents of each of these applications are incorporated herein by reference in their entireties.

FEDERALLY SPONSORED RESEARCH AND DEVELOPMENT

This invention was made with Government support under contract AA011147 awarded by the National Institutes of Health. The Government has certain rights in the invention.

BACKGROUND

Endometriosis is identified as one of the few disorders in women's health research with little progress in the last 20 years relative to screening, detection, prognosis, and treatment. The hallmark symptom of endometriosis is debilitating pain and on average, women experience pain ~10 years before being properly diagnosed. It is estimated 1 in 10 women (176 million people) of child-bearing age are affected by endometriosis.

Available treatments, including NSAIDS and opioids, are often ineffective or cannot provide long-term pain relief. Further, the gold standard of diagnosis is surgery to visually identify endometrial cysts and no diagnostic biomarkers exist to identify endometriosis that do not require an extensive invasive procedure. Disturbingly, in a United States National Health Interview Survey, half of the women with endometriosis reported being bedridden for ~17.8 days over a period of 12 months. Sixty percent of women with endometriosis reported that painful symptoms result in both physical and emotional limitations that significantly affected work-related activities. Women with endometriosis experience low energy (27%), depressed and discouraged mood (35%), and social life impairments (38%) secondary to their painful symptoms and have increased concern, worry, anxiety, self-blame, and financial and relationship difficulties. Women with endometriosis also experience emotions such as fear, anger, and depression and report feeling powerless, overwhelmed, and isolated all attributed to their painful symptoms. Unavoidably, this pain negatively impacts their relationships, self-esteem, social well-being, and feelings of control. Painful symptoms also negatively impact appetite, exercise, sleep, social activities, and child care-related activities. Therefore, there is an unmet need to develop improved diagnostic and targeted therapeutic strategies for women suffering from endometriosis.

Here, will describe a novel therapeutic strategy for endometriosis and endometriosis associated symptoms.

SUMMARY

Methods and compositions are provided for treating endometriosis in an individual. Aspects of the methods include administering to the individual an agent that promotes ALDH activity. Treatment may provide a reduction of endometrial tissue. Treatment may provide relief of, for example, dysmenorrhea, dyspareunia, dysuria, etc. Treatment may provide relief of pain associated with endometriosis.

In some embodiments the methods provide for administration of an effective dose of an ALDH promoting agent, which agent may include without limitation Alda-1 or an analog thereof, for example Alda-44, etc. In some embodiments administration is localized. In some embodiments administration is systemic. In some embodiments administration is localized by use of a pelvic, uterine, vaginal, etc. implant comprising an effective dose of an ALDH promoting agent, which implant is optionally although not necessarily a sustained release implant. Alternatively localized administration may utilize a gel, lotion, cream, etc. for topical administration, e.g. a vaginal or uterine administration, where an effective dose is delivered for temporary or sustained relief of pain.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A Five female Sprague-Dawley rats initially weighing 150-175 g were trained over a period of ~4 weeks to terminate an escape response from the noxious stimuli produced by a balloon inflated in the vagina. Top image: Rats trained to be accustomed to the testing chamber. Bottom image: The escape response assessed by the rat poking its head into a tube. This response in turn breaks an infrared beam and causes the vaginal balloon to deflate. FIG. 1B Once trained, one-hour testing sessions consist of seven distention volumes and one sham volume delivered to the balloon by a computer three times in random order at ~60 second intervals. Baseline vaginal nociceptive data were initially obtained for each rat and graphed as percent escape response as a function of vaginal distention volume (mL). The shaded area is calculated as the area under the curve. n=5 rats/volume FIG. 1C Histogram of vaginal escape response expressed as the area under the curve calculated using standard trapezoid methods. Testing sessions were performed every 3-4 days. The reactive aldehyde, acetaldehyde (9 mg/kg, diluted in saline; aldehyde in the figure), was delivered to the rat abdominal peritoneal cavity. Relative to saline, acetaldehyde significantly increased the percent escape response to vaginal distension and induces vaginal hyperalgesia. Alda-1 (1 mg/kg, intraperitoneal, diluted in DMSO), given 10 minutes before (Alda-1+aldehyde) or after acetaldehyde (aldehyde+Alda-1) prevented and reversed acetaldehyde-induced vaginal hyperalgesia. No effect was seen when Alda-1 or DMSO were given alone. *$P<0.01$ vs. saline or DMSO, +$P<0.01$ vs. acetaldehyde, using repeated measures one-way ANOVA with Bonferroni's multiple comparison test. All injections were delivered at a final volume of 250 μl. Data are presented as mean±SEM, n=5 rats/group.

FIG. 2A In a mouse surgical model of endometriosis, three (2 mm×2 mm) uterine horn auto transplants are sutured onto cascading mesenteric arteries which in turn since located outside the uterus develop cysts in the abdomen. FIG. 2B Female wild type (C57/BL6) and ALDH2*2 knock-in mice on the same genetic background 8-10 weeks of age were induced with endometriosis and sacrificed 1, 3, or 28 days later. Endometrial cysts were collected and cyst area was measured (length×width). FIG. 2C Average cyst area was calculated for each group (wild type: blue, ALDH2*2: red) of mice at day 1, 3, and 28. Data are presented as mean±SEM, n=6 mice/group.

FIG. 3A. Female wild type and ALDH2*2 C57/BL6 mice 8-10 weeks of age were surgically induced with endometriosis and treated for 3 or 28 days with Alda-1 (5 mg/kg, subcutaneous Alzet pump delivery, diluted in DMSO) or DMSO alone beginning the day of surgery. FIG. 3B. Example of endometrial cysts from wild type mice treated for 3 days with DMSO (top left) or Alda-1 (top right) and ALDH2*2 mice treated with DMSO (bottom left) or Alda-1 (bottom right). FIG. 3C. In endometriosis ALDH2*2 mice treated with Alda-1 for 3 days, average cyst area was significantly reduced relative to ALDH2*2 mice treated with DMSO. FIG. 3D. In endometriosis wild type and ALDH2*2 mice treated with Alda-1 for 28 days, average cyst area was significantly reduced relative to wild type and ALDH2*2 mice treated with DMSO, respectively. *$P<0.05$ vs. ALDH2*2 DMSO, +$P<0.05$ vs. WT DMSO, #$P<0.05$ vs. ALDH2*2 DMSO using one-way ANOVA with multiple comparisons and Bonferroni correction. All data are presented as mean±SEM, n=6 mice/group.

DETAILED DESCRIPTION OF THE INVENTION

Figure 1A:
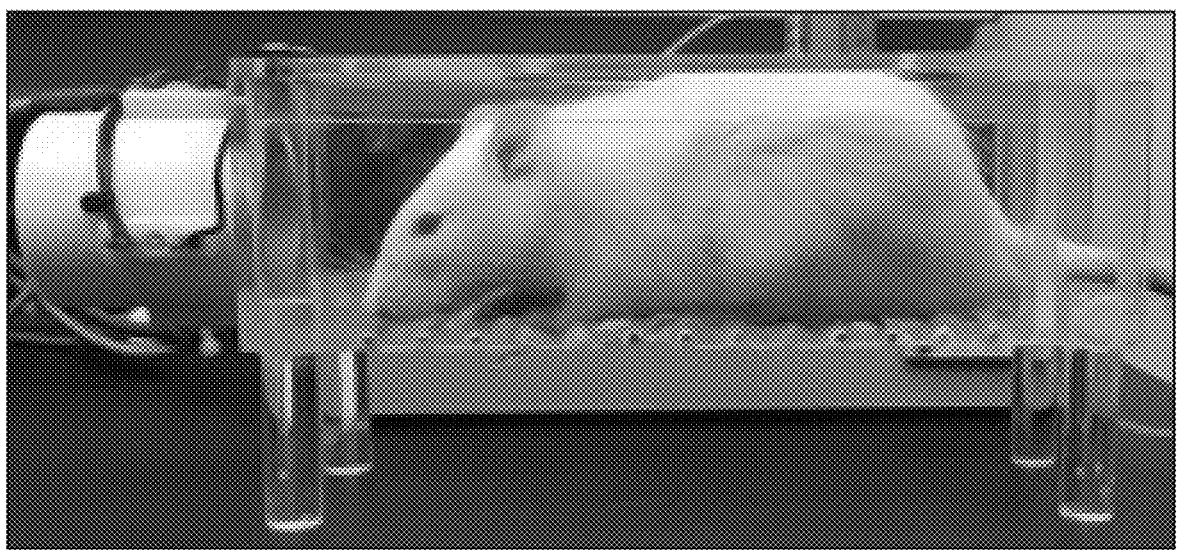
FIG. 1A-1C. Alda-1 mitigates acetaldehyde-induced vaginal hyperalgesia in rats.
Figure 1A:
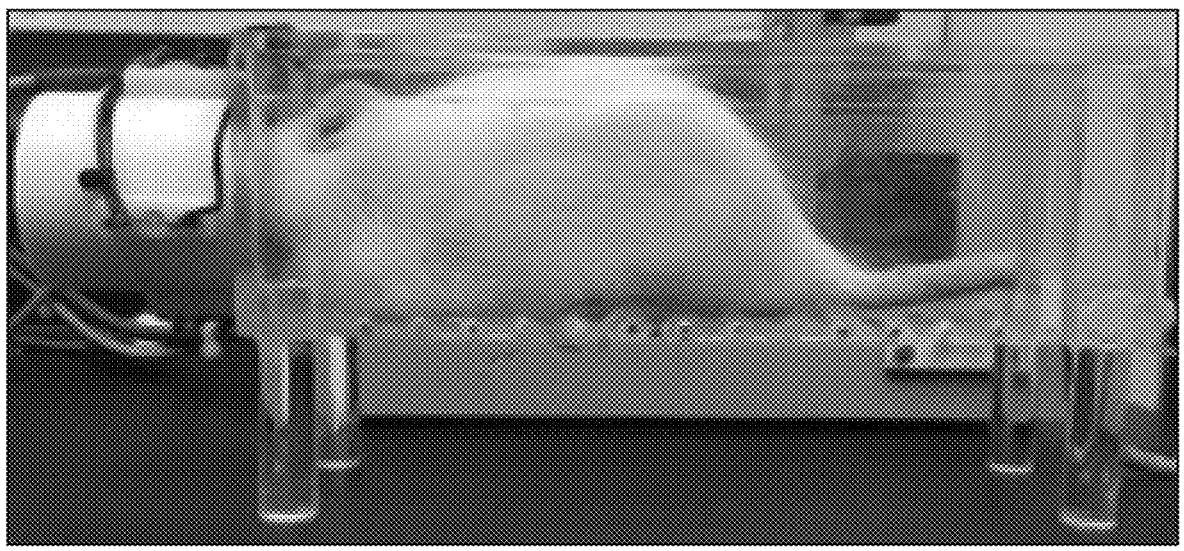

Methods and compositions are provided for treating endometriosis in an individual. Aspects of the methods include administering to the individual an agent that promotes ALDH activity. These methods find many uses, for example in treating and preventing pain; and in reducing endometrial tissue. These and other objects, advantages, and features of the invention will become apparent to those persons skilled in the art upon reading the details of the compositions and methods as more fully described below.

While not being bound by the theory, it is believed that Alda-1 may act through reducing oxidative stress. Oxidative stress is a known/significant factor in the pathogenesis, establishment, and progression of endometriosis. Alda-1, which increases ALDH2 activity and therefore reduces oxidative stress and subsequently improve aldehyde metabolism generated by oxidative stress, can reduce or eliminate the progression, establishment, etc of endometriosis. Specifically, in the mouse model of endometriosis, there is a peak in oxidative stress that occurs ~24 hours after endometriosis is induced. This peak in oxidative stress is thought to be responsible for changes in gene expression present by day 3 post-endometriosis induction and contribute to disease progression.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for treating endometriosis and pain associated with endometriosis in an individual. By "pain" or "algesia" it is meant the perception of any aversive or unpleasant sensation that originates from a specific region of the body.

Endometriosis, as used herein, thus includes the conditions commonly referred to as endometriosis externa (or endometriosis as defined in The Merck Manual) endometrioma, adenomyosis, adenomyoma, endometriotic or adenomyotic nodules of the uterosacral ligaments, endometriotic nodules elsewhere such as scar endometriosis, and any nonmalignant disorder in which functioning endometrial tissue is present at a locus other than the endometrium. As used herein, "endometriotic tissue" is endometrial tissue seen in endometriosis, that is, the endometrial tissue present in a location other than the endometrium of the uterus.

Endometriosis may be defined as a condition where functioning endometrial tissue is implanted in the pelvis outside the uterine cavity. Symptoms depend on location of the implants and may include dysmenorrhea, dyspareunia, infertility, dysuria, and pain during defecation. Diagnosis is by direct visualization and sometimes biopsy, usually via laparoscopy. Conventional treatments include anti-inflammatory drugs, drugs to suppress ovarian function and endometrial tissue growth, surgical ablation and excision of endometriotic implants, and, if disease is severe and no childbearing is planned, hysterectomy alone or hysterectomy plus bilateral salpingo-oophorectomy.

Endometriosis is usually confined to the peritoneal or serosal surfaces of pelvic organs, commonly the ovaries, broad ligaments, posterior cul-de-sac, and uterosacral ligaments. Less common sites include the fallopian tubes, serosal surfaces of the small and large intestines, ureters, bladder, vagina, cervix, surgical scars, and, more rarely, the lung, pleura, and pericardium.

Bleeding from peritoneal implants is thought to initiate sterile inflammation, followed by fibrin deposition, adhesion formation, and, eventually, scarring, which distorts peritoneal surfaces of organs, leading to pain and distorted pelvic anatomy. Reported prevalence varies but may be about 6 to 10% in all women; and 75 to 80% in women with chronic pelvic pain.

Microscopically, endometriotic implants consist of glands and stroma identical to intrauterine endometrium. These tissues contain estrogen and progesterone receptors and thus usually grow, differentiate, and bleed in response to changes in hormone levels during the menstrual cycle; also, these tissues can produce estrogen and prostaglandins. Implants may become self-sustaining or regress, as may occur during pregnancy. Ultimately, the implants cause inflammation and increase the number of activated macrophages and the production of proinflammatory cytokines.

Cyclic midline pelvic pain, specifically pain preceding or during menses (dysmenorrhea) and during sexual intercourse (dyspareunia), is typical and can be progressive and chronic (lasting >6 mo). Interstitial cystitis with suprapubic or pelvic pain, urinary frequency, and urge incontinence is common. Intermenstrual bleeding is possible.

Diagnosis of endometriosis is suspected based on typical symptoms but must be confirmed by direct visualization and sometimes biopsy, usually via pelvic laparoscopy but sometimes via laparotomy, vaginal examination, sigmoidoscopy, or cystoscopy. Biopsy is not required, but results may help with the diagnosis. Macroscopic appearance (eg, clear, red, brown, black) and size of implants vary during the menstrual cycle. However, typically, areas of endometriosis on the pelvic peritoneum are punctate red, blue, or purplish brown spots that are >5 mm, often called powder burn lesions. Microscopically, endometrial glands and stroma are usually present. Stromal elements in the absence of glandular elements indicate a rare variant of endometriosis called stromal endometriosis.

By "treatment", "treating" and the like it is generally meant obtaining a desired pharmacologic and/or physiologic effect, i.e. treatment of pain. The effect may be prophylactic in terms of completely or partially preventing pain or a symptom thereof and/or may be therapeutic in terms of a partial or complete relief from pain and/or adverse effects attributable to pain.

"Treatment" as used herein covers any treatment of endometriosis and endometrial-associated pain in a mammal. Treatment of endometriosis includes, for example, relieving the pain experienced by a woman suffering from endometriosis, and/or causing the regression or disappearance of endometriotic lesions. Treatment of pain may include (a) preventing pain from occurring in a subject which may be predisposed to pain but has not yet begun to feel it; (b) inhibiting pain, i.e., arresting its development; or (c) relieving pain, i.e., causing regression of, or relief from, pain. The therapeutic agent may be administered before, during or after the onset of pain, e.g. before, during or after the onset of the pain-inducing condition or injury. The treatment of ongoing pain, where the treatment stabilizes or reduces the pain of the patient, is of particular interest.

The terms "individual," "subject," "host," and "patient," are used interchangeably herein and refer to any mammalian subject for whom diagnosis, treatment, or therapy is desired, e.g. murine, rodent, canine, feline, equine, bovine, ovine, primate, human, etc., particularly human.

An "effective amount" of the therapeutic agent means a sufficient amount to effect "treatment" as defined. Treatment can be associated with undesirable effects ("side effects") along with the desired therapeutic effect, so that a medical practitioner prescribing or performing treatment will balance the potential benefits against the potential risks in determining what constitutes an appropriate"effective amount". Also, because the quantity of endometriotic tissue will vary from woman to woman, the "effective amount" to be administered can vary. The skilled medical practitioner can determine an appropriate "effective amount" in any individual case.

By "hyperalgesia" it is mean a decrease in the threshold required to trigger an action potential in a nociceptor, i.e. the nociceptor is sensitized such that a low intensity stimulus initiates a painful sensation. There are several different types of pain that are recognized in the art. These include, for example, nociceptive pain, inflammatory pain, and neuropathic pain. In other words, the sensation of pain in response to a stimulus is enhanced. By "inflammatory pain" it is meant pain due to nociceptor stimulation by immune cells during an inflammatory response. Upon insult or injury to tissue (e.g. mechanical, thermal, chemical insult/injury, injury associated with neuropathy, etc.), the cells of the tissue may release factors, e.g. prostaglandins (e.g. PGE2), chemokines, etc. that promote the migration, adhesion and extravasation of leukocytes from the blood to the site of insult/injury. Recruited leukocytes in turn secrete inflammatory mediators, e.g. IL-1β, LIF, IL-6, Bradykinin, histamine, PGE2, 2-AG, 5-HT, etc., and reactive oxygen species, some of which stimulate nociceptor terminals while promoting the propagation and maturation of the inflammatory response. Thus, inflammatory pain is typically accompanied by inflammation and swelling, e.g. edema, at the site of pain. In some instances, the inflammation may produce hyperalgesia. Hyperalgesia may occur at the site of tissue damage (primary hyperalgesia) and/or in the surrounding undamaged areas (secondary hyperalgesia).

Nonlimiting examples of pain that may be treated by the subject methods include nociceptive pain, inflammatory pain, or neuropathic pain relating to endometriosis. The pain may be acute pain, i.e. pain that arises as an awareness of noxious signaling from recently damaged tissue, sometimes complicated by sensitization in the periphery and/or within the CNS. Alternatively, the pain may be chronic pain, i.e. pain without apparent biological value that has persisted beyond the normal tissue healing time (usually taken to be three months).

Methods of Treatment

In some aspects of the subject methods, endometriosis is treated by providing an agent that promotes, i.e. enhances or augments, aldehyde dehydrogenase activity in the individual. In other words, an agent that promotes aldehyde dehydrogenase activity is an analgesic. By "aldehyde dehydrogenase activity" it is meant the activity of enzymes that oxidize (dehydrogenate) aliphatic and aromatic aldehydes to carboxylic acids in an NAD+- or NADP+-dependent reaction. In some aspects, pain may be treated by providing an agent that promotes, i.e. enhances or augments, the activity of an aldehyde dehydrogenase (ALDH), i.e. an ALDH agonist.

By an "aldehyde dehydrogenase", or "ALDH", it is meant an enzyme that belongs to the well-known family of enzymes with pyridine-nucleotide-dependent oxidoreductase activity. ALDHs catalyze the oxidation (dehydrogenation) of a wide spectrum of aliphatic and aromatic aldehydic substrates (e.g., a xenogenic aldehyde, a biogenic aldehyde, or an aldehyde produced from a compound that is ingested, inhaled, or absorbed) to carboxylic acids in an NAD$^+$- or NADP$^+$-dependent reaction. For example, ALDH oxidizes aldehydes and acetaldehydes derived from the breakdown of compounds, e.g., toxic compounds that are ingested, that are absorbed, that are inhaled, or that are produced as a result of oxidative stress or normal metabolism, e.g., the metabolism of alcohol to acetaldehyde by alcohol dehydrogenase (ADH), the metabolism of retinol to retinal, etc. An aldehyde dehydrogenase can also exhibit esterase activity, i.e. the hydrolysis of esters, and/or reductase activity, e.g. the metabolism of glyceryl trinitrate (GTN) to 1,2-GDN and inorganic nitrite, which results in the formation of NO. ALDHs are isozymes. By isozymes it is meant enzymes that differ in amino acid sequence but catalyze the same chemical reaction. In other words, the enzymes are encoded by different genes, but process or catalyze the same reaction. These enzymes usually display different kinetic parameters (e.g. different KM values), or different regulatory properties.

ALDHs may be found in the cytosol, the mitochondria, microsome, and other cellular compartment. Examples of aldehyde dehydrogenases include members of the ALDH1 family, including ALDH1A1 (also known as ALDH1, ALDH-E1, ALDH11, and retinal dehydrogenase 1; see GenBank Accession No. NM_000689); ALDH1A2 (also known as RALDH2 or retinal dehydrogenase 2; see GenBank Accession Nos. NM_003888 (isoform 1), NM_170696.2 (isoform 2), NM_170696.2 (isoform 3), and NM_001206897 (isoform 4)); ALDH1A3 (also known as ALDH6, ALDH1A6, RALDH3, or retinal dehydrogenase 3; see Genbank Accession No. NM_000693); ALDH1B1 (also known as ALDH5 or ALDHX, see GenBank Accession No. NM_000692); ALDH1L1 (also known as FDH, FTHFD, or cytosolic 10-formyltetrahydrofolate dehydrogenase; see GenBank Accession Nos. NM_001270364 (isoform 1), NM_012190 (isoform 2), and NM_001270365 (isoform 3)); ALDH1L2 (also known as mtFDH or mitochondrial 10-formyltetrahydrofolate dehydrogenase, see GenBank Accession No. NM_001034173); members of the ALDH2 family, in particular ALDH2 (see GenBank Accession Nos. NM_000690 (isoform 1) and NM_001204889 (isoform 2); members of the ALDH3 family, e.g. ALDH3A1 (also known as ALDH3; see GenBank Accession No. NM_001135168.1 (variant 1), NM_000691.4 (variant 2), and NM_001135167.1 (variant 3)); ALDH3A2 (also known as ALDH10, FALDH, or fatty aldehyde dehydrogenase; see GenBank Accession Nos. NM_001031806.1 (isoform 1) and NM_000382.2 (isoform 2)); ALDH3B1 (also known as ALDH4; ALDH7; see GenBank Accession Nos. NM_000694.2 (isoform a) and NM_001030010.1 (isoform b)); ALDH3B2 (also known as ALDH8; see GenBank Accession Nos. NM_000695.3 (variant 1) and NM_001031615.1 (variant 2)); members of the ALDH4 family, particularly ALDH4A1 (also known as ALDH4; P5CD; GenBank Accession Nos. NM_003748.3 (isoform a) and NM_001161504.1 (isoform b)); members of the ALDH5 family, particularly ALDH5A1 (also known as SSDH, or succinate-semialdehyde dehydrogenase, mitochondrial; see GenBank Accession Nos. NM_170740.1 (isoform 1) and NM_001080.3 (isoform 2)); members of the ALDH6 family, particularly ALDH6A1 (also known as MMSDH or methylmalonate-semialdehyde dehydrogenase [acylating], mitochondrial; see GenBank Accession No. NM_005589.2); members of the ALDH7 family, particularly ALDH7A1 (see GenBank Accession Nos. NM_001182.4 (isoform 1), NM_001201377 (isoform 2), and NM_001202404 (isoform 3)); members of the ALDH8 family, particularly ALDH8A1 (also known as ALDH12; see GenBank Accession Nos. NM_022568.3 (isoform 1), NM_170771.2 (isoform 2) and NM_001193480.1 (isoform 3); members of the ALDH9 family, particularly ALDH9A1 (also known as E3, ALDH4, ALDH7, ALDH9, TMABADH or 4-trimethylaminobutyraldehyde dehydrogenase; see GenBank Accession No. NM_000696.3); members of the ALDH16 family, particularly ALDH16A1 (see GenBank Accession Nos. NM_153329.3 (isoform 1) and NM_001145396.1 (isoform 2); and members of the ALDH18 family, particularly ALDH18A1 (GSAS, P5CS, PYCS, ARCL3A, or delta-1-pyrroline-5-carboxylate synthase; see GenBank Accession Nos. NM_002860.3 (isoform 1) and NM_001017423.1 (isoform 2)). An ALDH polypeptide can exhibit one or more of the following enzymatic activities: a) a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid); b) an esterase activity; and c) a reductase activity. More information regarding the members of the ALDH family of proteins may be found on the world wide web by typing in "www" followed by "aldh.org".

The term "ALDH" is used herein to encompass any known native ALDH polypeptide or variant thereof. By "native polypeptide" it is meant a polypeptide found in nature. For example, native ALDH polypeptides include any human ALDH as described herein, the sequences for which may be found at the GenBank Accession Numbers described herein, as well as ALDH homologs that naturally occur in humans and ALDH orthologs that naturally occur in other eukaryotes, e.g. in mice, rodents, canines, cats, equines, bovines, primates. By "variant" it is meant a mutant of the native polypeptide having less than 100% sequence identity with the native sequence. For example, a variant may be a polypeptide having 60% sequence identity or more with a full length native ALDH, e.g. 65%, 70%, 75%, or 80% or more identity, such as 85%, 90%, or 95% or more identity, for example, 98% or 99% identity with the full length native ALDH. Variants also include fragments of a native ALDH polypeptide that have aldehyde dehydrogenase activity, e.g. a fragment comprising residues 18-517 of ALDH2 or the comparable sequence in an ALDH homolog or ortholog. Variants also include polypeptides that have aldehyde dehydrogenase activity and 60% sequence identity or more with a fragment of a native ALDH polypeptide, e.g. 65%, 70%, 75%, or 80% or more identity, such as 85%, 90%, or 95% or more sequence identity, for example, 98% or 99% identity with the comparable fragment of the native ALDH polypeptide.

Human ALDHs are provided here as examples of native ALDH polypeptides, but it will be appreciated by the ordinarily skilled artisan that native ALDH polypeptides from any eukaryote and variants thereof may be employed in the treatment of pain, these native ALDH polypeptides being readily identified using publicly available resources such as PubMed or NCBI Blast. The aldehyde dehydrogenase activity of these ALDH polypeptides in mitotic cells can be readily confirmed by any convenient method for detecting the oxidation of aldehydes to carboxylic acids in an NAD+-dependent or an NADP+-dependent reaction, e.g. as known in the art or as described herein. The term "ALDH polypeptide" encompasses a polypeptide having a length of from about 400 amino acids to about 600 amino acids (aa), e.g., from about 400 aa to about 450 aa, from about 450 aa to about 500 aa, from about 500 aa to about 550 aa, or from about 550 aa to about 600 aa.

In some embodiments, an agent that promotes ALDH activity promotes a dehydrogenase activity of ALDH, that is, the agent promotes dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, an agent that promotes ALDH activity promotes an esterase activity of ALDH. In other embodiments, an agent that promotes ALDH activity promotes a reductase activity of ALDH. For example, ALDH can convert nitroglycerin to nitric oxide (NO) via its reductase activity.

In some embodiments, a subject ALDH agonist promotes, i.e. enhances or augments, the enzymatic activity of a particular ALDH isozyme. For example, in some embodiments, a subject ALDH agonist promotes, i.e. enhances or augments, the enzymatic activity of the aldehyde dehydrogenase ALDH2. "ALDH2" or "mitochondrial aldehyde dehydrogenase-2" is a mitochondrial matrix homotetramer with broad specificity and a low $K_m$ for acetaldehydes. ALDH2 is a member of the ALDH1B subfamily of ALDHs and is localized to the mitochondrial matrix. Human ALDH2 has a sequence disclosed in GenBank Accession Nos. NM_000690 (isoform 1) and NM_001204889 (isoform 2); a mouse ALDH2 amino acid sequence is found under GenBank Accession No. NP_033786; and a rat ALDH2 amino acid sequence is found under GenBank Accession No. NP_115792. The term "ALDH2" encompasses an aldehyde dehydrogenase that exhibits substrate specificity, e.g., that preferentially oxidizes aliphatic aldehydes. The term "ALDH2" encompasses an enzymatically active polypeptide having at least about 75%, at least about 80%, at least about 85%, at least about 90%, at least about 95%, at least about 98%, at least about 99%, or 100%, amino acid sequence identity to amino acids 18-517 of the amino acid sequence set forth in SEQ ID NO:1. The term "ALDH2" as used herein also encompasses fragments, fusion proteins, and variants (e.g., variants having one or more amino acid substitutions, addition, deletions, and/or insertions) that retain ALDH2 enzymatic activity, e.g. 1% or more enzymatic activity, 2% or more enzymatic activity, 5% or more enzymatic activity, 10% or more enzymatic activity, 20% or more enzymatic activity, 30% or more enzymatic activity, 50% or more enzymatic activity, 80% or more enzymatic activity, 90% or more enzymatic activity, or 100% enzymatic activity, i.e. the enzymatic activity of the variant is no different from that of native ALDH2. Enzymatically active ALDH2 variants, fragments, fusion proteins, and the like can be verified by adapting the methods described herein. One example of an ALDH2 variant is ALDH2*2 (SEQ ID NO:2), wherein a lysine residue replaces a glutamate in the active site at position 487 of processed human ALDH2 (residue 504 of unprocessed ALDH2, SEQ ID NO:1), or at a position in a non-human ALDH2 corresponding to amino acid 487 of human ALDH2. This mutation is referred to as the "E487K mutation"; the "E487K variant"; or the "Glu504Lys polymorphism". See, e.g., Larson et al. (2005) J. Biol. Chem. 280:30550; and Li et al. (2006) J. Clin. Invest. 116:506. Individuals that are homozygous for ALDH2*2 have almost no ALDH2 activity, and those heterozygous for the mutation have reduced activity.

Any convenient agent that promotes the activity of an ALDH (i.e. any "ALDH agonist"), or more particularly, ALDH2 (i.e. any "ALDH2 agonist"), may be employed as an analgesic, i.e. to treat pain in the subject methods. For example, an ALDH agonist that finds use in the subject methods may increase the amount of ALDH in a cell, or may activate or increase the activity of an ALDH, e.g. by activating an ALDH directly or by promoting the activity of proteins upstream of ALDH, etc. So, for example, when it is desirable to treat pain by administering an agent that promotes the activity of ALDH2, the subject methods will encompass agents that increase the amount of ALDH2 in a cell, or that activate or increase the activity of ALDH2 or a variant thereof, e.g. by activating ALDH2 or variant thereof directly or by promoting the activity of proteins upstream of ALDH2, etc.

For example, agents that are small molecule compounds find use in the subject methods. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992). Small molecule compounds can be provided directly to the medium in which the cells are being cultured, for example as a solution in DMSO or other solvent.

As another example, agents that would be suitable for use in the subject methods include nucleic acids, for example, nucleic acids that encode ALDH polypeptides or active fragments thereof. Many vectors useful for transferring nucleic acids into target cells are available. The vector may be maintained episomally, e.g. as plasmid, minicircle DNA, virus-derived vector such as cytomegalovirus, adenovirus, etc., or it may be integrated into the target cell genome, through homologous recombination or random integration, e.g. retrovirus derived vectors such as MMLV, HIV-1, ALV, etc. The nucleic acid agent may be provided directly to the cells. In other words, the cells are contacted with vectors comprising the nucleic acid of interest such that the vectors are taken up by the cells. Methods for contacting cells with nucleic acid vectors, such as electroporation, calcium chloride transfection, and lipofection, are well known in the art. Alternatively, the nucleic acid agent may be provided to cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the subject cells are targeted by the packaged viral particles. Methods of introducing the retroviral vectors comprising the nucleic acid ALDH agonist into packaging cell lines and of collecting the viral particles that are generated by the packaging lines are well known in the art.

Vectors used for providing nucleic acid of interest to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by 5 fold or more, by 10 fold or more, by at least about 100 fold or more, more usually by at least about 1000 fold. In addition, vectors used for providing nucleic acid to the subject cells may include genes that must later be removed, e.g. using a recombinase system such as Cre/Lox, or the cells that express them destroyed, e.g. by including genes that allow selective toxicity such as herpesvirus TK, bcl-xs, etc Agents suitable for promoting ALDH activity in the present invention also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. Polypeptides may be fused to a polypeptide permeant domain to promote the transport of the polypeptide agent across the cell membrane and into the cell. A number of permeant domains are known in the art and may be used in the polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The polypeptide agent for use in the subject methods may be produced from eukaryotic produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

For example, when it is desirable to promote the activity of ALDH2, any convenient agent that promotes the enzymatic activity of ALDH2 may be employed. One example of such an agent is a functional ALDH polypeptide or functional fragment or variant thereof, e.g. an ALDH2 polypeptide, a functional polypeptide or fragment thereof of the isozyme ALDH1, etc. Specific enzymatically active ALDH2 polypeptide variants, fragments, fusion proteins, and the like can be verified by adapting the methods described herein. Another example is a small molecule allosteric activator of ALDH2, e.g. Alda-1 (N-(1,3-benzodioxol-5-ylmethyl)-2,6-dichlorobenzamide) or an analog thereof, e.g. the water soluble derivative Alda-44. Other examples of ALDH2 agonists include those disclosed in US applications US20090082431, US20100063100, US 20100113423, and U.S. Pat. No. 7,560,241, the full disclosures of which are herein incorporated by reference.

Whether a compound is an ALDH agonist can be readily ascertained. Assays for dehydrogenase activity of ALDH are known in the art, and any known assay can be used. Examples of dehydrogenase assays are found in various publications, including, e.g., Sheikh et al. ((1997) J. Biol. Chem. 272:18817-18822); Vallari and Pietruszko (1984) J. Biol. Chem. 259:4922; and Farres et al. ((1994) J. Biol. Chem. 269:13854-13860).

As an example of an assay for dehydrogenase activity, ALDH aldehyde dehydrogenase activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes NAD+ (e.g., 0.8 mM NAD+, or higher, e.g., 1 mM, 2 mM, or 5 mM NAD+) and an aldehyde substrate such as 14 µM propionaldehyde. Reduction of NAD+ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide (NAD+) to its reduced form, NADH, at 340 nm, as described in US 2005/0171043; and WO 2005/057213. In an exemplary assay, the reaction is carried out at 25° C. in 0.1 sodium pyrophosphate (NaPPi) buffer, pH 9.0, 2.4 mM NAD+ and 10 mM acetaldehyde as the substrate. Enzymatic activity is measured by a reductive reaction of NAD+ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043 and WO 2005/057213. Detection of fluorescent resorufin at 590 nm provides amplified and more sensitive signals for any change in ALDH aldehyde dehydrogenase enzymatic activity. NADP+ can be used in place of NAD+ in this assay. Suitable substrates include, but are not limited to, octylaldehyde, phenylacetaldehyde, retinaldehyde, and 4-hydroxynonenal. Any ALDH polypeptides (e.g., ALDH1, ALDH2, ALDH3, ALDH5, etc.) can be used. The enzyme used in the assay can be purified (e.g., at least about 75% pure, at least about 80% pure, at least about 85% pure, at least about 90% pure, at least about 95% pure, at least about 98% pure, or at least about 99% pure). Recombinant ALDH enzyme can also be used in the assay.

As another example, the effect of a compound on aldehyde dehydrogenase activity of an ALDH polypeptide can be assayed as described in Wierzchowski et al. ((1996) Analytica Chimica Acta 319:209), in which a fluorogenic synthetic substrate, e.g., 7-methoxy-1-naphthaldehyde is used. For example, the reaction could include 7-methoxy-1-naphthaldehyde, NAD+, an ALDH polypeptide, and an ALDH agonist to be tested; fluorescence (excitation, 330 nm; emission 390 nm) is measured as a readout of enzymatic activity.

Whether a compound increases an esterase activity of ALDH can be determined using any known assay for esterase activity. For example, esterase activity of ALDH2 can be determined by monitoring the rate of p-nitrophenol formation at 400 nm in 25 mM N,N-Bis (2-hydroxyethyl)-2-amino ethanesulfonic acid (BES) (pH 7.5) with 800 µM p-nitrophenyl acetate as the substrate at room temperature in the absence or presence of added NAD+. A pH-dependent molar extinction coefficient of 16 mM-1 cm-1 at 400 nm for nitrophenol can be used. See, e.g., Larson et al. (2007) J. Biol. Chem. 282:12940). Esterase activity of ALDH can be determined by measuring the rate of p-nitrophenol formation at 400 nm in 50 mM Pipes (pH 7.4) with 1 mM p-nitrophenylacetate as the substrate. A molar extinction coefficient of 18.3×103 M−1 cm−1 at 400 nm for p-nitrophenolate can be used for calculating its rate of formation. See, e.g., Ho et al. (2005) Biochemistry 44:8022).

Whether a compound increases a reductase activity of ALDH can be determined using any known assay for reductase activity. A reductase activity of ALDH can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 ml in ethanol for subsequent TLC separation and scintillation counting. See, e.g., Zhang and Stamler (2002) Proc. Natl. Acad. Sci. USA 99:8306.

In some embodiments, a subject ALDH agonist is specific for (e.g., selective for) ALDH2, e.g., a subject ALDH2 agonist increases an enzymatic activity of an ALDH2 enzyme, but does not substantially increase the same enzymatic activity of cytosolic aldehyde dehydrogenase-1 (ALDH1), e.g., a subject ALDH2 agonist increases an enzymatic activity of an ALDH1 enzyme, if at all, by less than about 15%, less than about 10%, less than about 5%, less than about 2%, or less than about 1%, when used at a concentration that increases the same enzymatic activity of an ALDH2 enzyme by at least about 5% or more. In some embodiments, a subject ALDH2 agonist does not substantially increase the enzymatic activity of alcohol dehydrogenase (ADH), e.g., a subject ALDH2 agonist increases the enzymatic activity of an ADH, if at all, by less than about 5%, less than about 2%, or less than about 1%, when used at a concentration that increases the enzymatic activity of an ALDH2 enzyme by at least about 5% or more.

For example, in some embodiments, a subject ALDH2 agonist is specific for (e.g., selective for) ALDH2, e.g., a subject ALDH2 agonist increases dehydrogenase activity of an ALDH2 enzyme, but does not substantially increase the dehydrogenase activity of cytosolic aldehyde dehydrogenase-1 (ALDH1), e.g., a subject ALDH2 agonist increases dehydrogenase activity of an ALDH1 enzyme, if at all, by less than about 15%, less than about 10%, less than about 5%, less than about 2%, or less than about 1%, when used at a concentration that increases dehydrogenase activity of an ALDH2 enzyme by at least about 5% or more. In some embodiments, a subject ALDH2 agonist does not substantially increase dehydrogenase activity of alcohol dehydrogenase (ADH), e.g., a subject ALDH2 agonist increases the dehydrogenase activity of an ADH, if at all, by less than about 5%, less than about 2%, or less than about 1%, when used at a concentration that increases the dehydrogenase activity of an ALDH2 enzyme by at least about 5% or more.

In some embodiments, a subject ALDH agonist increases an enzymatic activity of certain ALDH enzymes, e.g. the isozymes ALDH1 and ALDH2, but does not substantially increase the same enzymatic activity of any other ALDH enzyme, e.g., a subject ALDH agonist increases an enzymatic activity of an ALDH isozyme other than ALDH1 and ALDH2 by 15% or less, by 10% or less, by 5% or less, by 2% or less, by 1% less, e.g. by a negligible amount, if at all, when used at a concentration that increases the same enzymatic activity of an ALDH1 and ALDH2 enzyme by at least about 15% or more.

The agent that promotes ALDH activity (the "ALDH agonist") is typically provided to cells in a therapeutically effective amount. By a "therapeutically effective amount" or "efficacious amount" it is meant an amount of an agent that, when administered to a mammal or other subject for treating pain, is sufficient, either alone in one or more doses, or in combination in one or more doses with another agent, to prevent such pain or to effect such relief for the pain, i.e. to reduce the pain, to achieve analgesia for the pain; to reduce endometrial tissues, etc. The "therapeutically effective amount" will vary depending on the compound, the cause of the pain and its severity and the age, weight, etc., of the subject to be treated.

A therapeutically effective amount or effective dose of an ALDH agonist may be the dose that, when administered for a suitable period of time, usually at least 5 minutes or more, e.g. 15 minutes or more, 1 hour or more, 2 hours or more, or 3 hours or more, in some instances 4 hours or more, 5 hours or more, or 6 hours or more, sometimes 12 hours or more or 24 hours or more, will evidence an alteration in the responsiveness of an individual to endometrial pain. For example, a therapeutically effective amount or effective dose of an ALDH agonist (or ALDH2 agonist) is the dose that, when administered for a suitable period of time, usually at least about 5 minutes or more, e.g. 15 minutes or more, one hour or more, 2 hours or more, or 3 hours or more, in some instances 4 hours or more, 5 hours or more, or 6 hours or more, sometimes 12 hours or more or 24 hours or more, will increase the pain threshold by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, or at least about 10-fold. In some instances, the ALDH agonist may be prophylactically therapeutic, e.g. the therapeutically effective amount will be the amount sufficient to prevent pain, for example when delivered prior to the condition that would result in pain, or after the onset of the condition that would result in pain but prior to the onset of pain. In some instances, the ALDH agonist may be administered after the onset of pain, in which case the therapeutically effective amount will be the amount sufficient to reduce the sensation of pain by at least about 5%, at least about 10%, at least about 15%, or at least about 20%, in some cases by at least about 25%, at least about 30%, at least about 35%, at least about 40%, at least about 45%, at least about 50%, or at least about 60%, more usually at least about 70%, at least about 80%, at least about 90% or at least about 98% (i.e. to negligible amounts), in some instance by 100%, in other words, rendering the person free of pain. It will be understood by those of skill in the art that this effect may be achieved by a single dose or by multiple doses. A reduction in pain may occur via an increase in ALDH2 activity that ultimately reduces reactive aldehyde levels.

In some embodiments the therapeutic dose of an ALDH agonist is the dose that, when administered for a suitable period of time, is sufficient to shrink endometrial tissue by at least 10% relative to untreated, at least 25%, at least 50%, at least 75% or more. It may be noted that endometrial cyst size (or amount of ectopic tissue) may not predict or correlate with the presence of or severity of painful symptoms, with the exception of deep infiltrating endometriosis (DIE) in which growths/cysts/adhesions are deeply embedded and often compress nerves to generate pain.

The therapeutically effective dose may be readily determined using any convenient preclinical or clinical assay e.g. as known in the art or described herein in the Examples. For example, in a preclinical setting, pain threshold may be assessed in an animal administered an ALDH agonist using a paw pressure test or von Frey test. Such results are typically compared to the results from a control, or reference, sample, e.g. an animal not administered the ALDH agonist. In a clinical setting, pain may be measured on a quantitative or a qualitative scale. Any convenient method may be used to measure pain in such instances. For example, pain may be measured on the visual analogue scale (VAS), the numerical rating scale (NRS), the verbal descriptor scale (VDS). Methods particularly useful in children and the infirm include the FLACC (i.e. face, Legs, Activity, Cry, and Consolability) Behavior Pain Scale, the Touch Visual Pai (TVP) Scale, the Wong-Baker FACES Pain Rating Scale, and the Pain Thermometer. See, e.g., "Guide to Pain Management in Low-Resourse Settings", A. Kopf and N. B. Patel, eds., IASP, Seattle, © 2010. In some embodiments, the method further comprises measuring the pain felt by the individual and determining that the pain has been reduced following treatment with the agent as compared to before administration of the agent. For shrinkage of endometrial cysts, monitoring may occur by pelvic ultrasound or by magnetic resonance imaging (MRI).

Biochemically speaking, an therapeutically effective amount or effective dose of an ALDH agonist will be the amount required to increase the enzymatic activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH polypeptide in the absence of the agonist. In certain embodiments, the ALDH polypeptide is an ALDH2 polypeptide or variant thereof.

In some embodiments, an effective amount of a subject ALDH agonist is the amount effective to increase a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH polypeptide in the absence of the agonist. In certain embodiments, the ALDH polypeptide is an ALDH2 polypeptide or variant thereof.

In some embodiments, an effective amount of a subject ALDH agonist is the amount effective to increase the esterase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH polypeptide in the absence of the agonist. In certain embodiments, the ALDH polypeptide is an ALDH2 polypeptide or variant thereof.

In some embodiments, an effective amount of a subject ALDH agonist is the amount effective to increase the reductase activity of an ALDH polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH polypeptide in the absence of the agonist. In certain embodiments, the ALDH polypeptide is an ALDH2 polypeptide or variant thereof.

The extent to which ALDH enzymatic activity is modulated by an ALDH agonist can be readily determined by any convenient way known to one of ordinary skill in the art of molecular biology or neurobiology or as described herein. For example, ALDH enzymatic activity may be determined spectrophotometrically by monitoring the reductive reaction of NAD+ to NADH at A340 nm in the presence of acetaldehyde. As another example, the presence and concentration of aldehyde adducts, e.g. 4-Hydroxinonenal (4-HNE) protein adducts, in tissue may be assessed by Western blotting using an antibody specific for HNE amino acid adducts (Calbiochem, NJ) In this way, the agonistic effect of the agent may be confirmed.

Calculating the effective amount or effective dose of ALDH agonist to be administered is within the skill of one of ordinary skill in the art, and will be routine to those persons skilled in the art. Needless to say, the final amount to be administered will be dependent upon a variety of factors, include the route of administration, the nature of the disorder or condition that is to be treated, and factors that will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally or topically administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

An ALDH agonist may be administered to an individual by any of a number of well-known methods in the art or described herein for the administration of small molecules, peptides, and nucleic acids to a subject. The ALDH agonist can be incorporated into a variety of formulations. More particularly, the ALDH agonist of the present invention can be formulated into pharmaceutical compositions by combination with appropriate pharmaceutically acceptable carriers or diluents, and may be formulated into preparations in solid, semi-solid, liquid or gaseous forms, such as gels, tablets, capsules, powders, granules, ointments, solutions, suppositories, injections, inhalants, gels, microspheres, and aerosols. As such, administration of the ALDH agonist can be achieved in various ways, including oral, vaginal, buccal, parenteral, intraperitoneal, intradermal, transdermal, etc., administration. The active agent may be systemic after administration or may be localized by the use of regional administration, intramural administration, or use of an implant that acts to retain the active dose at the site of implantation, e.g. in vaginal gel or implant. The active agent may be formulated for immediate activity or it may be formulated for sustained release.

The calculation of the effective amount or effective dose of ALDH agonist to be administered is within the skill of one of ordinary skill in the art, and will be routine to those persons skilled in the art. Needless to say, the final amount to be administered will be dependent upon the route of administration, upon the nature of the pain that is to be treated, the health and physical condition of the individual to be treated, age, the taxonomic group of individual to be treated (e.g., human, non-human primate, primate, etc.), the degree of resolution desired, the formulation of the ALDH agonist composition, the treating clinician's assessment of the medical situation, and other relevant factors. It is expected that the amount will fall in a relatively broad range that can be determined through routine trials. For example, the amount of ALDH agonist employed to treat pain is not more than about the amount that could otherwise be irreversibly toxic to the subject (i.e., maximum tolerated dose). In other cases the amount is around or even well below the toxic threshold, but still in an effective concentration range, or even as low as threshold dose.

Individual doses are typically not less than an amount required to produce a measurable effect on the individual, and may be determined based on the pharmacokinetics and pharmacology for absorption, distribution, metabolism, and excretion ("ADME") of the ALDH agonist or of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic effects, or local effects when retained in part of the digestive tract), or parenteral (applied by routes other than the digestive tract for systemic or local effects) applications. For instance, administration of the ALDH agonist may be via injection, e.g. intravenous, intramuscular, intracranial, or intraventricular injection, or a combination thereof.

The ALDH agonist may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 6 hours, about 12 hours, about 24 hours, or about 48 hours to about once every several days, for example, about every five days, etc.

Where the agonist is Alda-1 or a derivative thereof, the effective dose may range from about 1 µg/kg weight to about 100 mg/kg body weight, for example from about 1 µg/kg, from about g/kg, from about 10 µg/kg, from about 25 µg/kg, from about 50 µg/kg, from about 100 µg/kg, from about 250 µg/kg, from about 500 µg/kg, from about 750 µg/kg, from about 1 mg/kg, from about 2.5 mg/kg, from about 5 mg/kg, from about 7.5 mg/kg, from about 10 mg/kg, from about 15 mg/kg, from about 20 mg/kg, from about 25 mg/kg, up to about 100 mg/kg, up to about 75 mg/kg, up to about 50 mg/kg, up to about 25 mg/kg, up to about 10 mg/kg, up to about 5 mg/kg, up to about 1 mg/kg or any range in between.

The ALDH agonist may be administered by intralesional administration, i.e. administration into or within a pathological area. Administration is effected by injection into a lesion and/or by instillation into a pre-existing cavity, such as in endometrioma. With reference to treatments for endometriosis provided herein, intralesional administration refers to treatment within endometriotic tissue or a cyst formed by such tissue, such as by injection into a cyst. "Intralesional administration" also includes administration into tissue in such close proximity to the endometriotic tissue such that the progestogen acts directly on the endometriotic tissue, but does not include administration to tissue remote from the endometriotic tissue that the progestogen acts on the endometriotic tissue through systemic circulation. Intralesional administration or delivery includes transvaginal, endoscopic or open surgical administration including, but are not limited to, via laparotomy. Delivery may be transvaginal, which refers to all procedures, including drug delivery, performed through the vagina, including intravaginal delivery and transvaginal sonography (ultrasonography through the vagina).

The ALDH agonist can also be administered prior, at the time of, or after other therapeutic interventions, e.g. the administration of other analgesics, the administration of therapeutics directed at the cause of the pain, surgical intervention, etc. The ALDH agonist can also be administered as part of a combination therapy, in which at least one of an immunotherapy, a hormone therapy including, for example, also is administered to the subject.

Currently available medical therapies are designed to suppress estrogen synthesis, inducing atrophy of ectopic endometriotic implants or interrupting the cycle of stimulation and bleeding. Oral contraceptive, androgenic agents, progestins and gonadotropin-releasing hormone analogues have all been successfully used in the treatment of endometriosis. Unfortunately, these hormonal treatments are often associated with unwanted effects caused by a hypo-estrogenic state. An ideal treatment for endometriosis induces regression of the disease and its symptoms without any adverse effects associated with a hypo-estrogenic state. Where a therapy is combined with administration of an ALDH agonist, the combined therapy may utilize lower doses or shorter time periods for administration relative to the use of the therapy without an ALDH agonist.

Combined therapies may include, without limitation, oral or intrauterine progestins, e.g. levonorgestrel-releasing intrauterine device; GnRH antagonists, e.g. cetrorelix, abarelix, etc.; aromatase inhibitors, e.g. anastrozole, letrozole, etc.; selective estrogen receptor modulators (SERMs), e.g. raloxifene, etc.; progesterone antagonists, e.g. mifepristone, onapristone, etc.; selective progesterone receptor modulators (SPRM), e.g. asoprisnil; angiogenesis inhibitors, e.g. TNP470, endostatin, anginex, rapamycin, thalidomide, etc.; immunomodulators, e.g. loxoribine, IFN-α 2 β and TNF-α inhibitors, pentoxifylline; matrix metalloproteinase inhibitors, e.g. doxycycline, 5-fluorouracil; thiazolidinediones, metformin; and the like.

Disposition of the ALDH agonist and its corresponding biological activity within a subject is typically gauged against the fraction of ALDH agonist present at a target of interest. Thus dosing regimens in which the ALDH agonist is administered so as to accumulate in a target of interest over time can be part of a strategy to allow for lower individual doses. This can also mean that, for example, the doses of ALDH agonist that are cleared more slowly in vivo can be lowered relative to the effective concentration calculated from in vitro assays (e.g., effective amount in vitro approximates mM concentration, versus less than mM concentrations in vivo).

As an example, the effective amount of an ALDH agonist can be gauged from the $EC_{50}$ of a given ALDH agonist concentration. By "$EC_{50}$" is intended the plasma concentration required for obtaining 50% of a maximum effect in vivo. In related embodiments, dosage may also be determined based on $ED_{50}$ (effective dosage).

In general, with respect to the subject methods, an effective amount of ALDH agonist is usually not more than 100× the calculated $EC_{50}$. For instance, the amount of a ALDH agonist that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $EC_{50}$ can be calculated by modulating the enzymatic activity of the ALDH polypeptide, e.g. the aldehyde dehydrogenase activity, in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and illustrated in the Experimental section, below. For example, if a concentration used for carrying out the subject method in mice ranges from about 1 mg/kg to about 25 mg/kg based on the body weight of the mice, an example of a concentration of the ALDH agonist that can be employed in human may range about 0.083 mg/kg to about 2.08 mg/kg. Other dosage may be determined from experiments with animal models using methods known in the art (Reagan-Shaw et al. (2007) *The FASEB Journal* 22:659-661).

The ALDH agonist can be incorporated into a variety of formulations. More particularly, the ALDH agonist may be formulated into pharmaceutical compositions by combination with appropriate pharmaceutically acceptable carriers or diluents.

Pharmaceutical preparations are compositions that include one or more ALDH agonists present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the ALDH agonist can be achieved in various ways, including transdermal, intradermal, oral, buccal, rectal, parenteral, intraperitoneal, intradermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For inclusion in a medicament, the ALDH agonist may be obtained from a suitable commercial source. As a general proposition, the total pharmaceutically effective amount of the ALDH agonist administered parenterally per dose will be in a range that can be measured by a dose response curve.

ALDH agonist-based therapies, i.e. preparations of ALDH agonist to be used for therapeutic administration, may be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The ALDH agonist-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection. Alternatively, the ALDH agonist may be formulated into lotions for topical administration.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatment of pain. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapies that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

In some embodiments, the agent that promotes ALDH activity may be administered alone, e.g. in the absence of other therapeutic agents. In other embodiments, the ALDH agonist may be administered in combination with other agents, e.g. other analgesics, e.g. NSAIDS, COX-2 inhibitors, etc., or may be administered in conjunction with other therapies, e.g. surgical interventions.

Utility

The subject methods find many uses for treating pain associated with endometriosis in an individual and for reducing endometrial tissue. It is shown in the working examples herein that the administration of an ALDH agonist reduces the sensitivity to pain and hyperalgesia in an animal model for endometriosis, and reduces the levels of aldehydes that have been shown by others to promote pain; and reduces the size of endometrial cysts.

The agent may be administered prior to, for example, intercourse, e.g. 5 minutes or more, 15 minutes or more, 30 minutes or more, 45 minutes or more, 1 hour or more, 2 hours or more, 3 hours or more, 4 hours or more, 5 hour or more, or 6 hours or more, and typically not more than 6 hours before, e.g. as a prophylactic, e.g., to prevent pain following insult/injury to the tissue. In other embodiments, the agent is administered after the onset of pain, e.g. 5 minutes or more, 10 minutes or more, 15 minutes or more, 20 minutes or more, 30 minutes or more, 45 minutes or more, 1 hour or more, 2 hours or more, 3 hours or more, 4 hours or more, 5 hours or more, 6 hours or more, 12 hours or more, or 24 hours or more after the onset of pain.

In some embodiments, the subject methods find use in treating pain promoted by aldehydes, e.g. acetaldehyde, 4-hydroxy-2-nonenal (4-HNE), etc. i.e. aldehyde-mediated pain. Elevated levels of aldehydes, e.g., 4-HNE, or protein adducts thereof, e.g. HNE adducts, e.g. in blood/plasma, in a tissue biopsy, etc., may be measured using any convenient method, for example, GC-MS (Spies-Martin et al. J. Chromatogr B Analyt Technol Biomed Life Sci 2002. 774(2): 231-9), ELISA (e.g. OxiSelect™ HNE Adduct ELISA kit), labeling with a fluorescent probe such as 2-aminopyridine (2-AP) (Wakiti et al. Free Radic Biol Med 2011. 51(1):1-4), etc.

In some instances, the subject methods may be used to treat a human for endometriosis. In some embodiments, a human to be treated according to a subject method is one that has two "wild-type" or "native" ALDH2 alleles, e.g., the ALDH2 encoded by the two wild-type ALDH2 alleles has a glutamic acid at position 487. In other embodiments, a human to be treated according to a subject method is one that has one or two hypomorphic alleles. By a "hypomorphic allele" it is meant that the allele encodes a variant of the protein with reduced activity relative to the level of activity of the wild type. One example of a hypomorphic allele is the "ALDH2*2" allele, i.e. the ALDH2 allele that encodes a polypeptide comprising a lysine as amino acid position 487 of SEQ ID NO:2. In some embodiments, the ALDH2 encoded by one or both ALDH2 alleles comprises a lysine as amino acid position 487. The E487K polymorphism is a semidominant polymorphism, and results in an ALDH2 tetramer that has significantly lower enzymatic activity than "wild-type" ALDH2. Thus, individuals who are heterozygous or homozygous for the ALDH2*2 allele have much lower in vivo ALDH2 activity levels than individuals who are homozygous for the "wild-type" ALDH2 allele. Individuals who are heterozygous or homozygous for the ALDH2*2 allele are expected to benefit from treatment with a subject ALDH2 agonist, because the level of ALDH2 activity in such individuals is particularly low, and any increase of ALDH2 activity levels would be expected to provide a therapeutic effect.

Individuals having an ALDH2 hypomorphic allele may be identified by any convenient method in the art for detecting such mutations. For example, where a subject is genotyped for an ALDH2 single nucleotide polymorphism (SNP), e.g. the ALDH2*2 polymorphism, a subject or patient sample, e.g., cells or collections thereof, e.g., tissues, is assayed to determine the nucleotide sequence of the gene at that polyporphism, or the amino acid sequence encoded by the gene at that polymorphism, e.g., by using one or more genotyping reagents, such as but not limited to nucleic acid reagents, including primers, etc., which may or may not be labeled, as described below, amplification enzymes, buffers, etc. In practicing the subject methods, the sample obtained from the subject is assayed to determine the genotype of the subject from which the sample was obtained with respect to at least one, i.e., one or more, polymorphisms, where polymorphisms of interest are referred to herein as target polymorphisms, examples of which are mentioned above. Any convenient protocol for assaying a sample for the above one or more target polymorphisms may be employed in the subject methods. In certain embodiments, the target polymorphism will be detected at the protein level, e.g., by assaying for a polymorphic protein. In yet other embodiments, the target polymorphism will be detected at the nucleic acid level, e.g., by assaying for the presence of nucleic acid polymorphism, e.g., an single nucleotide polymorphism (SNP) that cause expression of the polymorphic protein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Endometriosis is an estrogen-dependent disease characterized by the growth of endometrial tissue (ectopic growths) outside the uterus. The hallmark symptom of endometriosis is pain which can include pain during intercourse, menstruation, defecation, and/or chronic pelvic visceral and muscle pain. Another symptom, infertility, can affect up to 50% of women with endometriosis. A validated rodent model of endometriosis produces ectopic endometrial cysts and symptoms similar to that of women including vaginal hyperalgesia, referred abdominal pain, and infertility. This experimental rodent model is an excellent tool to develop diagnostic and therapeutic strategies for endometriosis.

Malondialdehyde (MDA) and 4-hydroxynonenal (4-HNE) are chemically classified as reactive aldehydes which are highly diffusible into cells. Reactive aldehydes exert cellular toxicity by causing Michael-addition adduct formation on proteins at cysteine (sulfhydryl), lysine (e-amino), or histidine (imidazole) amino acids. These reactive aldehyde protein adducts produce functional changes in enzyme activity, ion channel gating, and mitochondrial energetics. Under oxidative stress, human blood levels of the reactive aldehyde 4-HNE can increase 10-100-fold. Similar increases are also seen in MDA. In rodents, direct application of these aldehydes causes pain. The mitochondrial enzyme aldehyde dehydrogenase-2 (ALDH2) is essential in metabolizingreactive aldehydes into less cytotoxic unreactive forms. Recently, we discovered that reactive aldehydes produced with inflammation mediate pain. Further, Alda-1, a novel mitochondrial aldehyde dehydrogenase (ALDH2) activator, increases the efficiency of reactive aldehyde metabolism and increases pain thresholds in rodent models of inflammatory pain.

Here we describe the efficacy of ALDH2 enzymatic activators as an effective strategy in alleviating endometriosis associated pain and as a disease modifier for endometriosis. The strategies include: A means to shrink or reduce endometrial cyst size. A means to reduce abdominal pain associated with endometriosis. A means to reduce pain associated with sexual intercourse. A means to use aldehyde levels as a biomarker in the blood or in the exhaled breath to identify women with endometriosis. A means to treat infertility. A means to improve energy in women with endometriosis.

Figure 1B:
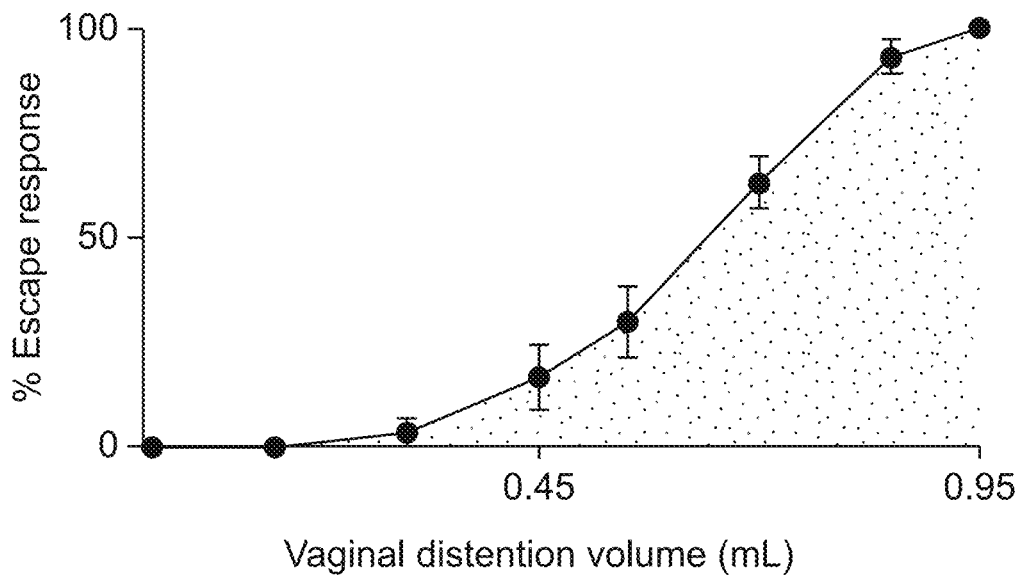

Alda and endonetriosis: Although rodent inflammatory pain models such as carageenan and CFA may represent some aspects of endometriosis, there is a validated rat model of endometriosis-associated pain, which produces signs and painful symptoms similar to those in women (S. McAllister, K. McGinty, D. Resuehr, K. Berkley. Endometriosis-induced vaginal hyperalgesia in the rat: Role of the ectopic growths and their innervation. *Pain.* 147: 255-264 (2009)). We therefore have begun determining the effect of Alda-1 in female rodents, using this model for endometriosis-associated pain. In this model, female Sprague-Dawley rats were trained to perform an escape response to a noxious stimulus delivered to the vagina. Similar to the painful symptom of dyspareunia in women with endometriosis, this model assesses vaginal hyperalgesia. To this end, a balloon that is inserted in the vagina is inflated to a specific volume. The rat is then monitored to determine an escape response, which is assessed by the rodent breaking an infrared beam with its nose; this, in turn, causes the inflated balloon in the vagina to deflate (FIG. 1A). To establish baseline values, a computer program delivered randomly 7 volumes and 1 sham volume to the balloon in random order, 3 times each. We used these values to calculate a baseline area under the curve for each rodent tested (FIG. 1B, shaded portion of the figure). Note also that the experimenter in our study, is very experienced in using this model for over 10 years.

Figure 1C:
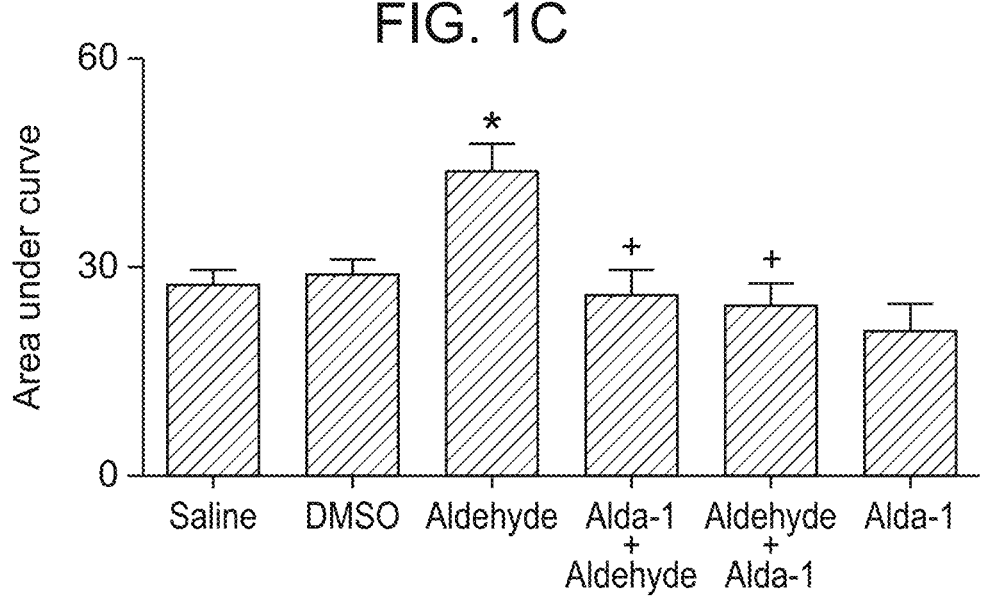

Next, we used acetaldehyde as the noxious stimulus. We previously demonstrated that inflammation results in acetaldehyde accumulation and that acetaldehyde injection causes hyperalgesia (V. O. Zambelli, E. R. Gross, C. H. Chen, V. P. Gutierrez, Y. Cury, D. Mochly-Rosen, Aldehyde dehydrogenase-2 regulates nociception in rodent models of acute inflammatory pain. *Sci Transl Med.* 6, 251 ra118 (2014). Therefore, as a first step in the model for endometriosis-induced pain, we injected acetaldehyde (9 mg/kg) into the intraperitoneal space in the right lower quadrant of the abdomen. When tested 10 minutes after acetaldehyde injection, acetaldehyde caused an increased sensitivity (hyperalgesia) to vaginal balloon distension (FIG. 1C, 44±4* vs. saline 28±2, *$P<0.05$). Importantly, when Alda-1 was given intraperitoneally 10 minutes prior to acetaldehyde, vaginal hyperalgesia was completely alleviated (FIG. 1C, 26±3+, +$P<0.05$ vs. acetaldehyde). Similar results were found when Alda-1 was given intraperitoneally 10 minutes after acetaldehyde injection (FIG. 1C, 25±3+, +$P<0.05$ vs. acetaldehyde). The reduction in acetaldehyde-induced vaginal hyperalgesia by Alda-1 was similar to control DMSO (the Alda-1 vehicle; FIG. 1C). Finally, relevant to the claim on the potential effect of Alda-1 as an inhibitor of ALDH2, in the absence of the noxious stimulus, Alda-1 had no effect in this assay (FIG. 1C). Current studies will determine whether Alda-1 is effective in other endometriosis-induced pain models.

Treatments for endometriosis-induced pain remain an unmet clinical need. We are therefore encouraged by our findings using intraperitoneal injection of acetaldehyde as a model of this hyperalgesia in addition to our rodent studies describing how treatment with Alda-1 can modulate the endometrial cysts formed. Our current study and previous report support our conclusion that Alda-1-like compounds show promise as novel therapeutics for inflammatory pain, in general, as well as for endometriosis-associated pain. Alda-1 may also offer a novel therapeutic which modifies the underlying disease condition by shrinking the endometrial cyst size.

Example 2

Female wild type C57/BL6 mice (n=36) and homozygous ALDH2*2 knock-in mice (n=36) 8-10 weeks old were surgically induced with endometriosis using the rat model developed by Vernon and Wilson (1985) and modified slightly by Cummings and Metcalf (1995). Briefly, mice were anesthetized with isoflurane (1-3%) and an off-midline (left side) incision made through the skin and muscle layer to expose the pelvic and abdominal organs. A ~1-cm segment of mid-left uterine horn with its attached fat was ligated proximally and distally with suture. The uterine horn was then excised and put in a sterile glass Petri dish containing ~100 μL of PBS containing penicillin (100 U/ml) and streptomycin (100 μg/ml). Three, 2 mm×2 mm pieces of the excised uterus (minus the fat) were then sutured onto alternate mesenteric arteries with nylon suture, the muscle layer closed with chromic gut suture, and the skin incision closed with non-absorbable polypropylene suture. An incision was then made at the nape of the mouse neck and an Alzet osmotic pump implanted for subcutaneous delivery of Alda-1 (5 mg/kg/day, diluted in DMSO) or DMSO alone (control). On day 1, 3, or 28 after endometriosis induction, mice were sacrificed, endometrial cyst length and width measured to calculate cyst area, and then the average cyst area per group determined.

Figure 2A:
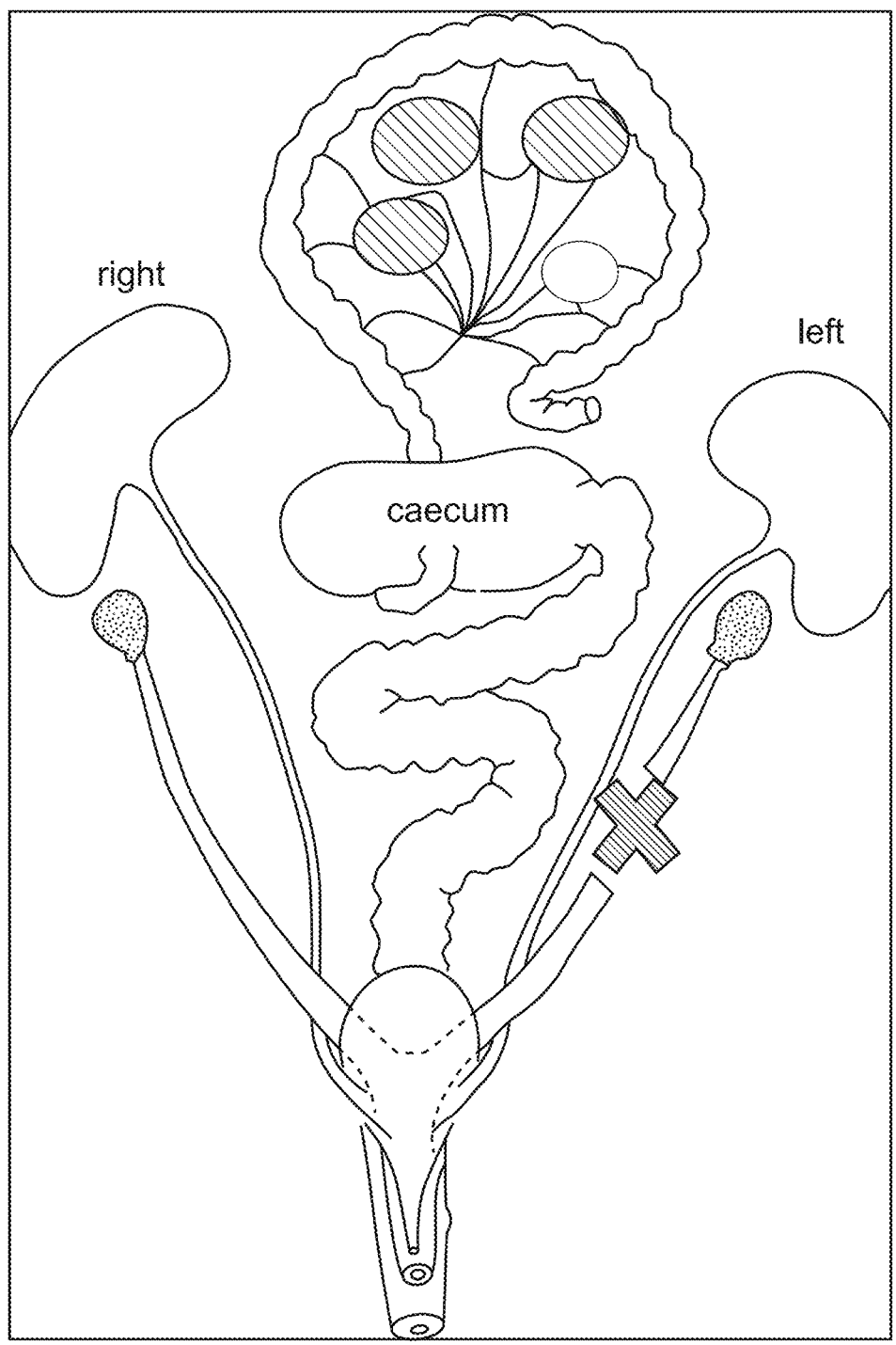
FIG. 2A-2C. Relative to wild type mice, ALDH2*2 mice develop larger endometrial cysts by 3 days after endometriosis surgery.
Figure 2B:
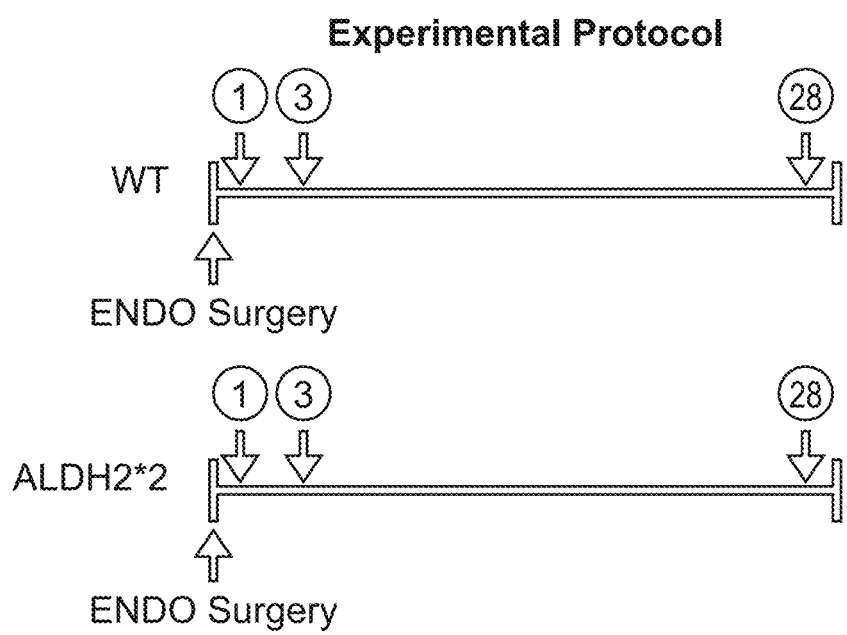
Figure 2C:
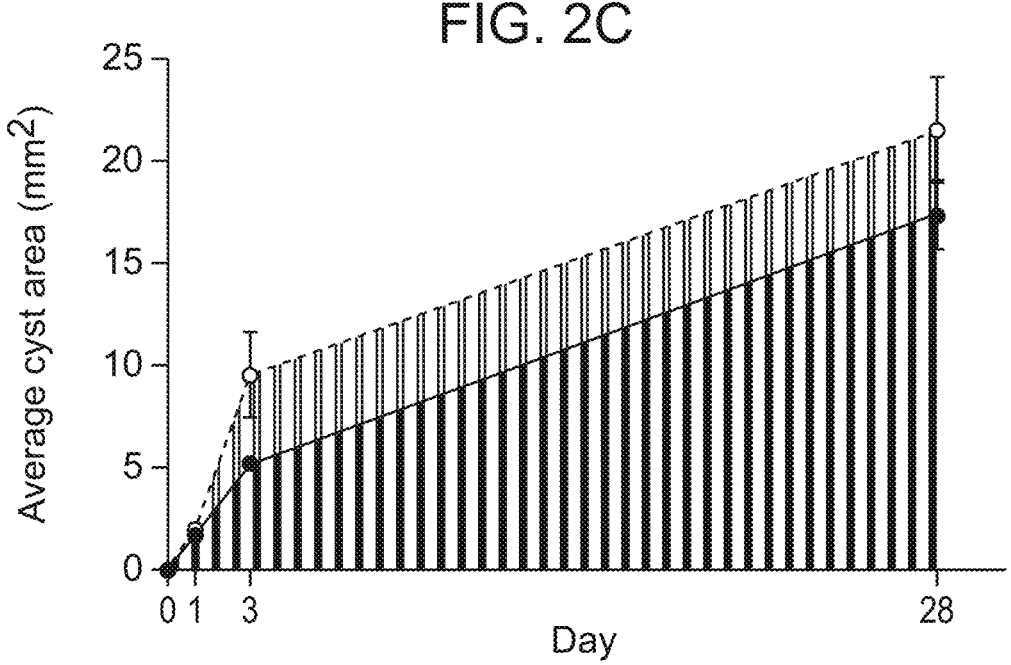
Figure 3A:
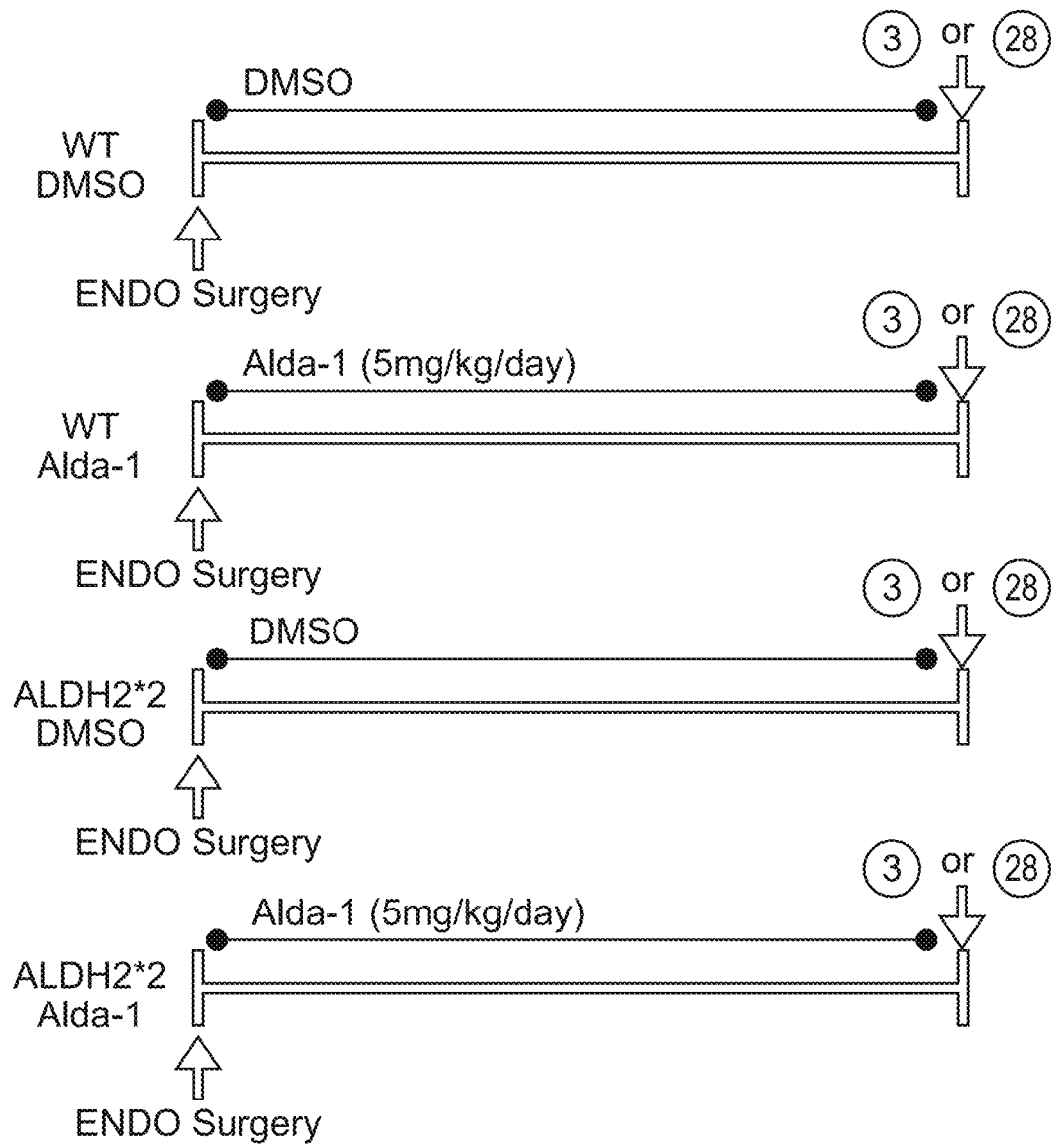
FIG. 3A-3D. Alda-1 reduces endometrial cyst size 3 days and 28 days after endometriosis induction.
Figure 3B:
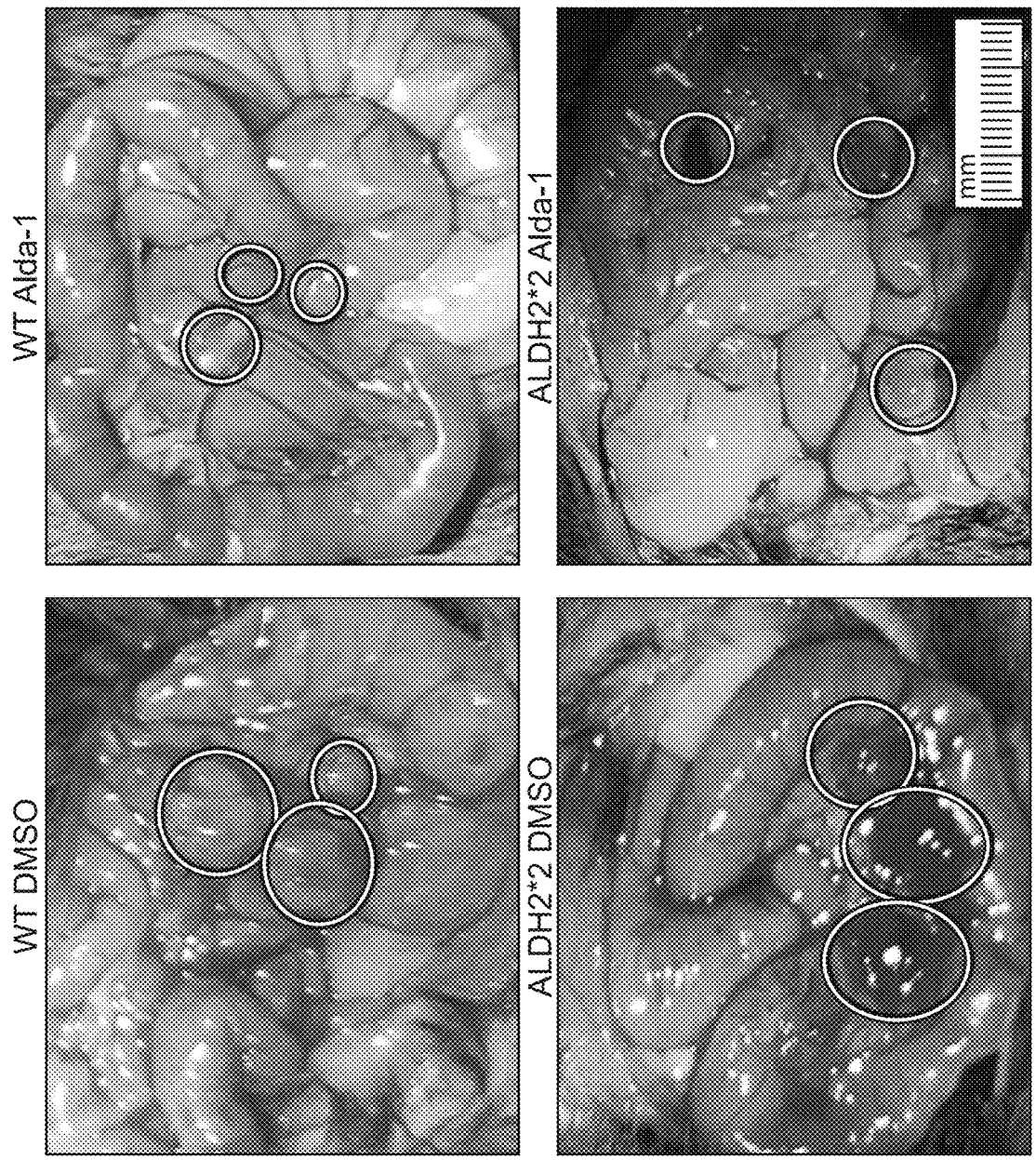
Figure 3C:
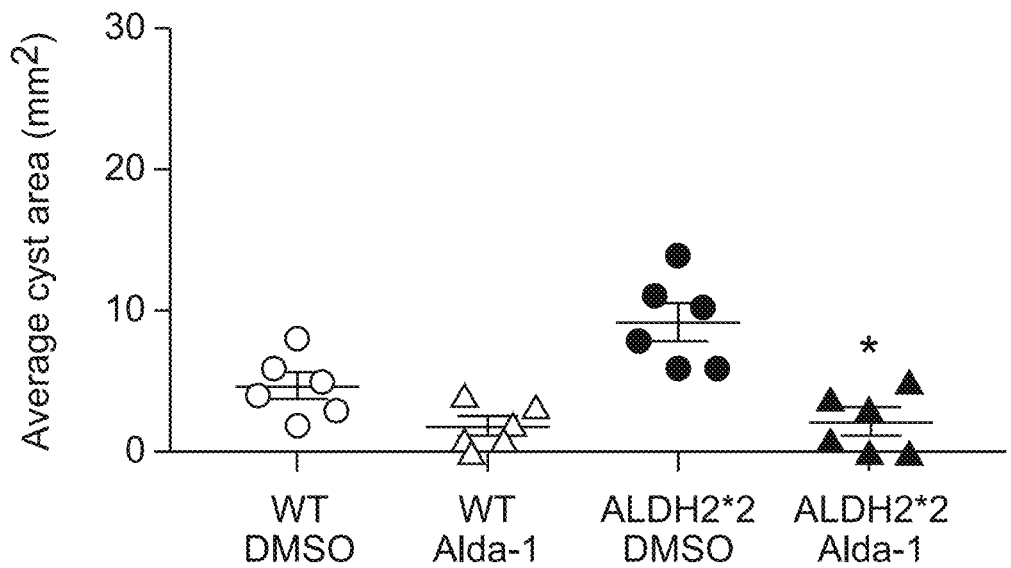
Figure 3D:
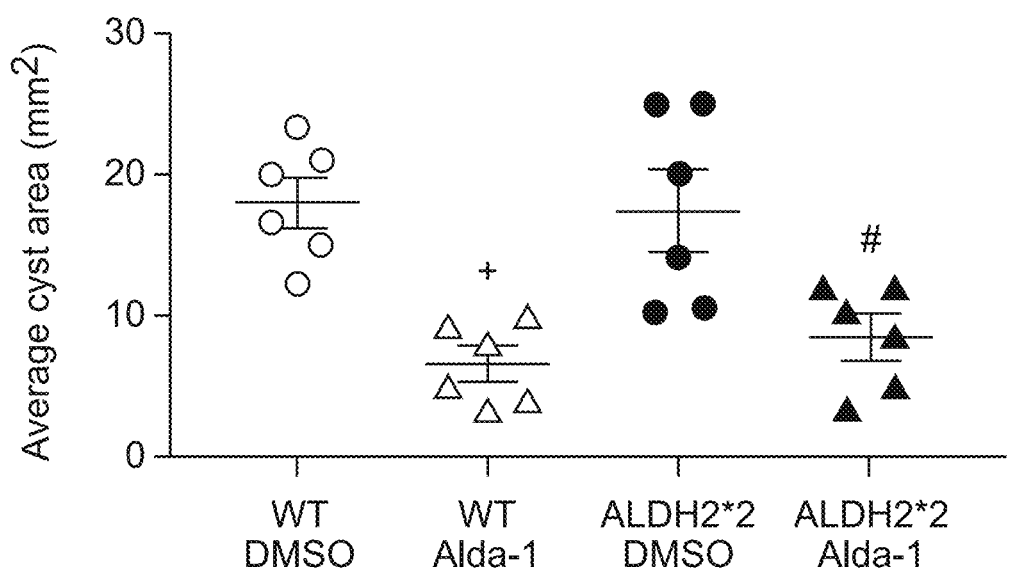

As shown in FIG. 2, relative to wild type mice, ALDH2*2 mice develop larger endometrial cysts by 3 days after endometriosis surgery. When treated with Alda-1, both wild type and ALDH2*2 mice showed a significant reduction in endometrial cyst size 3 days and 28 days after endometriosis induction, shown in FIG. 3. Treatment of Alda-1 or the vehicle control was delivered by subcutaneous Alzet pump delivery.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating endometriosis in a human individual, comprising:
    administering to the individual a dose of Alda-1 or Alda sufficient to shrink endometrial tissue by at least 10% relative to untreated tissue;
    wherein the treatment results in a reduction of endometrial tissue.

2. The method according to claim 1, wherein the individual has a hypomorphic mutation in ALDH2.

3. The method according to claim 2, wherein the mutation is ALDH2*2.

4. The method according to claim 1, wherein Alda-1 or Alda-44 is administered prior to the onset of pain.

5. The method of claim 1, wherein treatment is systemic.

6. The method of claim 1, wherein treatment is localized.

7. The method of claim 6, wherein treatment comprises providing a pelvic, uterine, or vaginal implant comprising an effective dose of Alda-1 or Alda-44 that promotes the activity of an aldehyde dehydrogenase.

8. The method of claim 6, wherein treatment comprising providing a pelvic, uterine, or vaginal lotion, gel or cream comprising an effective dose of Alda-1 or Alda-44 that promotes the activity of an aldehyde dehydrogenase for local administration.

9. A method of treating endometriosis in human individual, comprising:
    administering to the individual a dose of Alda-1 or Alda sufficient to shrink endometrial cysts by at least 10% relative to untreated tissue; and
    monitoring the individual for shrinkage of endometrial cysts,
    wherein the method of treating results in a shrinkage of endometrial cysts.

10. The method of claim 9, wherein monitoring is performed by pelvic ultrasound.

11. The method of claim 9, wherein monitoring is performed by magnetic resonance imaging (MRI).

12. The method of claim 9, wherein Alda-1 or Alda-4 is administered prior to onset of endometrial pain.

13. The method of claim 9, wherein treatment is systemic.

14. The method of claim 9, wherein treatment is localized.

15. The method of claim 14, wherein treatment comprises providing a pelvic, uterine, or vaginal implant comprising a dose of Alda-1 or Alda sufficient to shrink endometrial cysts by at least 10% relative to untreated tissue.

16. The method of claim 14, wherein treatment comprising providing a pelvic, uterine, or vaginal lotion, gel or cream comprising a dose of Alda-1 or Alda sufficient to shrink endometrial cysts by at least 10% relative to untreated tissue.

17. The method of claim 9, wherein the individual has a hypomorphic mutation in ALDH2.

18. The method of claim 17, wherein the mutation is ALDH2*2.

* * * * *

UNITED STATES PATENT AND TRADEMARK OFFICE
CERTIFICATE OF CORRECTION

| | | |
|---|---|---|
| PATENT NO. | : 11,974,981 B2 | Page 1 of 1 |
| APPLICATION NO. | : 17/681591 | |
| DATED | : May 7, 2024 | |
| INVENTOR(S) | : Eric Gross et al. | |

It is certified that error appears in the above-identified patent and that said Letters Patent is hereby corrected as shown below:

In the Specification

Please replace the entire paragraph in Column 1, starting at Line 18 with the paragraph below to read as follows:
-- GOVERNMENT SUPPORT RESEARCH
This invention was made with Government support under contracts AA011147, GM119522, and HD093858 awarded by the National Institutes of Health. The Government has certain rights in the invention. --

Signed and Sealed this
Fourth Day of November, 2025

John A. Squires
*Director of the United States Patent and Trademark Office*